United States Patent [19]

Eggersdorfer et al.

[11] Patent Number: 4,895,984
[45] Date of Patent: Jan. 23, 1990

[54] ACYLATION OF AROMATICS

[75] Inventors: Manfred Eggersdorfer, Frankenthal; Hardo Siegel, Speyer; Alfred Schuhmacher, Ludwigshafen; Walter Grosch, Edingen-Neckarhausen; Jochem Henkelmann, Mutterstadt, all of Fed. Rep. of Germany

[73] Assignee: BASF Aktiengesellschaft, Ludwigshafen, Fed. Rep. of Germany

[21] Appl. No.: 198,676

[22] Filed: May 25, 1988

Related U.S. Application Data

[63] Continuation of Ser. No. 54,574, May 27, 1987, abandoned.

[30] Foreign Application Priority Data

Jun. 6, 1986 [DE] Fed. Rep. of Germany ....... 3619169
Dec. 11, 1986 [DE] Fed. Rep. of Germany ....... 3642329

[51] Int. Cl.$^4$ .............................................. C07C 45/46
[52] U.S. Cl. .................................... 568/319; 568/323; 562/460
[58] Field of Search ................................. 568/319, 323

[56] References Cited

U.S. PATENT DOCUMENTS

| | | | |
|---|---|---|---|
| 2,004,069 | 6/1935 | Bruson et al. | 568/319 |
| 2,587,540 | 2/1952 | Shaver | 568/319 |
| 3,154,585 | 10/1964 | Flanagan | 568/323 |
| 4,087,458 | 3/1978 | Emori et al. | 560/219 |
| 4,310,705 | 1/1982 | Nissen et al. | 568/391 |

FOREIGN PATENT DOCUMENTS

| | | | |
|---|---|---|---|
| 0012850 | 11/1979 | European Pat. Off. | 568/391 |
| 1288584 | 2/1969 | Fed. Rep. of Germany | 568/391 |
| 2720294 | 8/1977 | Fed. Rep. of Germany | 560/219 |

OTHER PUBLICATIONS

Sneider et al., Tetrahedron, vol. 37, pp. 3927 to 3934 (1981).
Sneider et al., J. Org. Chem., vol. 47, pp. 5393–5395 (1982).
Reinheckel et al., J. Organometalic Chemistry, vol. 13, pp. 45–51 (1968).
Houben-Weyl, Methoden der Org. Chem., vol. VII/2a, 1973, pp. 15–39 and 311–325.
Friedel-Crafts and Related Reactions, vol. I, p. 207 and vol. III, Part I, pp. 550–553.

*Primary Examiner*—James H. Reamer
*Attorney, Agent, or Firm*—John H. Shurtleff

[57] ABSTRACT

Aromatics are acylated by the Friedel-Crafts method by carrying out the acylation in the presence of metalalkyls or metalalkyl halides of metals or semimetals of main groups two to five and/or of metals of subgroups two or four of the Periodic Table.

15 Claims, No Drawings

ACYLATION OF AROMATICS

This application is a continuation of application Ser. No. 54,574 filed May 27, 1987, now abandoned.

The present invention relates to an improved process for the acylation of aromatics by the Friedel-Crafts method, in particular for the preparation of alkyl-substituted aromatic ketones by reacting a carbonyl halide or carboxylic anhydride with an alkylaromatic in the presence of a Friedel-Crafts catalyst.

The, Friedel-Crafts acylation of aromatics, i.e. the introduction of an acyl group into aromatic compounds by the action of an acylating agent on aromatics in the presence of certain metal halides, for example aluminum chloride, is generally known, for example from Houben-Weyl, Methoden der org. Chem., vol. VII/2a, 1973, pages 15-39 and 311-325. The disadvantage of this process is the occurrence of side reactions, in particular when alkyl-substituted aromatics are acylated. For example, resinous byproducts are formed, the alkyl group is eliminated and isomerization occurs, especially when aromatics having secondary or tertiary alkyl radicals are reacted. According to various publications, these side reactions are supposed to be due to an interaction of $AlCl_3$ and hydrogen chloride, which, if not present in the catalyst, is formed during the Friedel-Crafts acylation (cf. C. A. Olah, Friedel-Crafts and Related Reactions, vol. I, page 207 and vol. III, Part I, page 550 et seq., Interscience 1964). In order to suppress the side reactions, it is recommended that freshly sublimed catalysts be used and the resulting hydrogen halide be removed from the reaction mixture by using reduced pressure or passing through an inert gas (cf. C. A. Olah, Friedel-Crafts and Related Reactions, vol. III, page 549, and literature cited there). Although the isomerization can to a certain extent be suppressed by these measures, as also disclosed in German Published Application DAS No. 2,720,294, the result is still unsatisfactory; further separation of the resulting product mixtures is complicated and in many cases cannot be carried out economically, so that the corresponding mixtures have to be used for subsequent reactions. Another disadvantage is that substantial amounts of the reactants are removed from the reaction mixture, resulting in poor yields.

It is an object of the present invention to improve the Friedel-Crafts acylation of aromatics in such a way that side reactions are substantially avoided and the products are obtained in high yields. In particular, it is intended to suppress the elimination and isomerization of the alkyl groups in the conversion of alkylaromatics.

We have found that this object is achieved by a process for the acylation of aromatics by the Friedel-Crafts method, wherein the acylation is carried out in the presence of a metalalkyl or metalalkyl halide of metals or semimetals of main groups two to five and/or metals of subgroups two or four of the Periodic Table.

The novel process can be particularly advantageously used for reacting carbonyl halides or carboxylic anhydrides with alkylaromatics to give alkyl-substituted ketones. Where (a) acetyl chloride or (b) phthalic anhydride and tert-butylbenzene are used as starting materials and a mixture of a metalalkyl or metalalkyl halide and aluminum chloride is used as the catalyst, the reaction can be represented by the following equations:

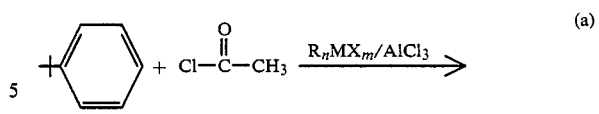

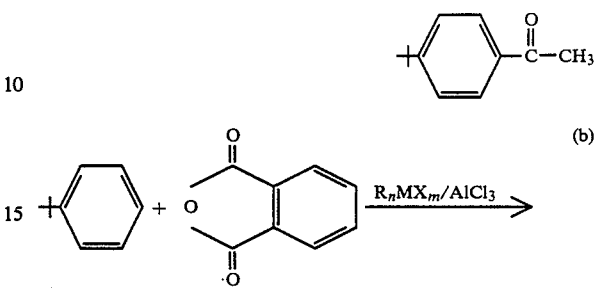

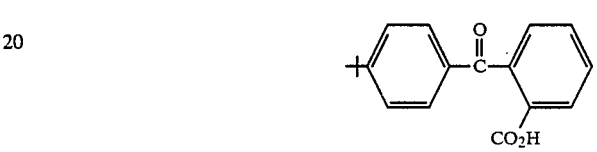

where R is alkyl, X is halogen, M is a metal or semimetal, n is from 1 to 4, m is from 0 to 4 and m+n is the valency of the metal.

According to the invention, the Friedel-Crafts acylation is carried out in the presence of effective amounts of metalalkyls or metalalkyl halides of metals or semimetals of main groups two to five, in particular three, of the Periodic Table and metals of subgroups two and/or four. They may be represented by the general formula $$R_nMX_m \qquad \text{I}$$

where the radicals R are identical or different alkyl groups of 1 to 12, preferably 1 to 6, in particular 1 to 4, carbon atoms, e.g. methyl, ethyl, n-propyl, isopropyl, n-butyl or isobutyl, M is a metal or semimetal of the stated groups, e.g. beryllium, magnesium, boron, gallium, indium, thallium, silicon, tin, lead, antimony, zinc, cadmium, mercury or titanium, X is fluorine, chlorine, bromine or iodine, for cost reasons chlorine frequently being preferred, n is from 1 to 4 and m is from 0 to 4, and the sum of n and m is the valency of the metal.

Mixtures of different compounds I can also be used.

The preparation of the organometallic compounds I can be carried out in a conventional manner, for example as described in Brockhaus ABC Chemie, 2 (1971), 867-869.

Particularly suitable compounds for the novel process are organometallic compounds of magnesium, such as dialkylmagnesium or Grignard compounds (RMgX), of boron, such as trialkylboron, dialkylboron halide or alkylboron dihalide, of tin, such as tetraalkyltin or trialkyltin halides, or of titanium, such as alkyltitanium trihalide or dialkyltitanium dihalide, and organozinc and organocadmium compounds, such as dialkylzinc or dialkylcadmium. Organozinc compounds are particularly preferably used. Aluminumalkyls and alkylaluminum halides, for example those of the formula Ia $$R_nAlX_{3-n} \qquad \text{Ia}$$

where the radicals R are identical or different alkyl groups of 1 to 12, preferably 1 to 6, in particular 1 to 4, carbon atoms, e.g. methyl, ethyl, n-propyl, isopropyl, n-butyl or isobutyl, X is fluorine, chlorine, bromine or iodine, for cost reasons chlorine being preferred, and n is 1, 2 or 3, or mixtures of two different compounds of the formula Ia are particularly preferred.

The following compounds are listed as examples: methylmagnesium chloride, ethylmagnesium bromide, diethyl-magnesium, trimethylboron, triethylboron, diethylboron chloride, diethylboron bromide, ethylboron dichloride, tetramethyltin, tetraethyltin chloride, methyltitanium trichloride, diethyltitanium dichloride, dimethylcadmium and in particular dimethylzinc, diethylzinc, dipropylzinc, dibutylzinc and ethylzinc chloride.

Particularly preferred compounds are methylaluminum dichloride and dibromide, ethylaluminum dichloride and dibromide, isopropylaluminum dibromide, n-hexyl-aluminum dichloride, dodecylaluminum diiodide, dimethyl-aluminum chloride, diethylaluminum bromide and dibutyl-aluminum iodide. Mixtures of these compounds are, for example, methylaluminum sesquichloride, ethylaluminum sesquichloride or mixtures of an alkylaluminum dichloride and a dialkylaluminum chloride in a molar ratio of, for example, from 20:1 to 1:20.

Instead of the alkylaluminum halides, trialkylaluminum, e.g. trimethyl-, triethyl-, tri-n-propyl-, triisopropyl-, tri-n-butyl- or tri-n-hexylaluminum, or aluminumalkyls having mixed alkyl radicals, e.g. methyldiethylaluminum, can also advantageously be added to the reaction mixture.

Suitable Friedel-Crafts catalysts are the conventional compounds, such as $FeCl_3$, $BF_3$, $ZnCl_2$ or $TiCl_4$. Aluminum halides, preferably aluminum bromide and in particular aluminum chloride, are particularly suitable.

Suitable aromatics are the compounds conventionally used for Friedel-Crafts reactions, such as isocyclic and heterocyclic aromatic hydrocarbons. In the novel process, alkylaromatics, e.g. alkyl-substituted benzenes, naphthalenes, anthracenes, furans, benzofurans, thiophenes etc., can particularly advantageously be reacted. Alkyl radicals are, for example, those of 1 to 20, in particular 1 to 12, preferably 1 to 8, carbon atoms. The alkyl radical and the aromatic nucleus may carry further substituents, such as halogen, e.g. chlorine or bromine, $C_1$-$C_4$-alkyl, $C_1$-$C_4$-alkoxy or hydroxyl; the alkyl radical may furthermore contain double or triple bonds. Alkylbenzenes having one or two branched or straight-chain alkyl radicals are preferably reacted. Examples of alkylbenzenes are: toluene, ethylbenzene, n-propylbenzene, isopropylbenzene, n-butylbenzene, sec-butylbenzene, tert-butylbenzene, n-pentylbenzene (2-methylbutyl)-benzene, (3-methylbutyl)-benzene, (1-methylbutyl)-benzene, (1,1-dimethylpropyl)-benzene, n-hexylbenzene, (1-ethyl-1-methylpropyl)-benzene, (1,1-dimethylbutyl)-benzene, (1-methylpentyl)-benzene, (1-ethyl-1-methyl)-benzene, (1-ethylhexyl)-benzene, oct-4-ylbenzene, 1,2-dimethylbenzene and 1,4-diethylbenzene.

The acylating agents used are the conventional compounds, in particular carbonyl halides and carboxylic anhydrides, as well as imide chlorides and the carboxylic acids themselves.

There are no restrictions with regard to the carbonyl halides or carboxylic anhydrides to be converted; for example, the acyl fluorides, iodides and in particular bromides and chlorides can be reacted. As a rule, the acyl chlorides of aliphatic, cycloaliphatic, araliphatic, aromatic and heterocyclic carboxylic acids are reacted. Acyl chlorides of the formula $R^1COCl$, where $R^1$ is hydrogen or an aliphatic radical, e.g. alkyl of 1 to 20, in particular 1 to 8, carbon atoms, unsubstituted or substituted aryl, preferably phenyl, which, where substituted, may carry in particular 1 or 2 substituents such as $C_1$-$C_4$-alkyl, aryloxy, such as phenoxy, halogen, such as fluorine, chlorine or bromine, or nitro, may be listed as examples. $R^1$ may furthermore be aralkyl, such as benzyl, or a heterocyclic radical, preferably an oxygen-containing or sulfur-containing heterocyclic radical having 5 or 6 ring members, e.g. furanyl, pyranyl or a thiophene radical.

Examples of acyl chlorides are the following: formyl chloride, acetyl chloride, propionyl chloride, n-butyryl chloride, n-octadecanoyl chloride, 3,3-dimethylacryloyl chloride, benzoyl chloride, 3-methoxybenzoyl chloride, 3-phenoxybenzoyl chloride, o-chlorobenzoyl chloride, 3-chloro-5-methylbenzoyl chloride, 2,6-dichlorobenzoyl chloride, m-bromobenzoyl chloride, o-bromobenzoyl chloride, p-methylbenzoyl chloride, p-tert-butylbenzoyl chloride, p-nitrobenzoyl chloride, p-carbomethoxybenzoyl chloride, m-carbobutoxybenzoyl chloride, phenylacetyl chloride, 4-chlorophenylacetyl chloride, cinnamyl chloride, 4-chlorocinnamyl chloride, furan-2-carbonyl chloride and thiophene-2-carbonyl chloride.

Suitable anhydrides are those of aliphatic, cycloaliphatic, araliphatic, aromatic or heterocyclic mono- or dicarboxylic acids. Anhydrides of monocarboxylic acids are, for example, those of alkylcarboxylic acids, such as acetic anhydride, propionic anhydride, n-butyric anhydride or benzoic anhydride. Anhydrides of dicarboxylic acids are, for example, those of the formula

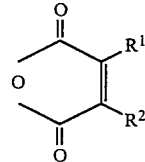

where $R^2$ has the same meanings as $R^1$ and furthermore $R^1$ and $R^2$ can be bonded to one another to form an unsubstituted or substituted aromatic ring system, for example a benzene ring. Examples are maleic anhydride, succinic anhydride, methylmaleic anhydride, tetraethylsuccinic anhydride, phthalic anhydride and 4,5-methylenedioxyphthalic anhydride.

Advantageously, stoichiometric amounts of the aromatic compound and the acylating agent can be used. However, it is also possible to use one of the two components in an excess compared with the other component; for example, from 1 to 1.5 moles of the aromatic can be used per mole of acylating agent.

The amounts of catalyst usually employed for Friedel-Crafts reactions may also be used in the novel process, the total amount of catalyst corresponding to the sum of the Lewis acid, such as aluminum halide, and the organometallic compound I.

The addition of the organometallic compound results in binding of the hydrogen chloride present or formed in the reaction mixture. The effective amount therefore depends on the number of alkyl radicals present in the molecule. The ratio of the isomerization products (for example, in the case of tert-amyl-substituted aromatics, the tertiary/secondary alkyl ratio) and the amount of byproducts can be influenced by the amount of metalalkyl or metalalkyl halide. As a rule, from 0.1 to about 1.1 equivalents of metalalkyl, in the form of the metalalkyl or metalalkyl halide, and from 0.1 to 1.5 moles of a Friedel-Crafts catalyst, e.g. an aluminum halide, can be added per equivalent of carbonyl halide, it being advantageous to use a small excess, e.g. a 10% excess, of the Friedel-Crafts catalyst. Larger excess amounts can be used but are of no advantage. In the case of carboxylic anhydrides or carbonyl halides which carry substituents which form stable complexes with Friedel-Crafts catalysts, e.g. aluminum halides and organometallic compounds, one equivalent of catalyst is additionally required per substituent.

In the preferred embodiment of the process, from 1 to 1.5, preferably from 1.1 to 1.2, moles of a mixture of a Friedel-Crafts catalyst and an alkylaluminum halide can be used per equivalent of acyl halide. If starting materials containing substituents which form stable complexes with the catalyst are used, the total amount of catalyst must be increased correspondingly. The effective amount of the organoaluminum compound is advantageously from 0.1 to about 1 mole of alkylaluminum dihalide, about 0.05–0.5 mole of dialkylaluminum halide or about 0.03–0.33 mole of trialkylaluminum, in each case per equivalent of carboxylic acid derivative, such as acyl halide or anhydride. Larger amounts up to complete replacement of the aluminum halide are possible, but for economic reasons the amount of organoaluminum compound is kept as small as possible.

The reaction can be carried out in the absence or, advantageously, in the presence of a solvent, suitable solvents being the conventional solvents for Friedel-Crafts reactions, for example chlorobenzene, dichlorobenzene, 1,2-dichloroethane, carbon disulfide, nitromethane or nitrobenzene. The amount of solvent is not critical; in general, from 200 to 1000 g of solvent can be used per mole of alkylbenzene.

The reaction can be carried out in a conventional manner, and the starting materials can be reacted at from −20° to 100° C., preferably from 0° to 60° C., in paticular from 10° to 40° C., under superatmospheric, reduced or, preferably, atmospheric pressure.

Advantageously, the carbonyl halide or carboxylic anhydride is initially taken together with the solvent, and the aluminum halide is added, followed by the alkylaromatic mixed with the metalalkyl or metalalkyl halide.

Working up of the reaction mixture and isolation of the products are carried out in a conventional manner, for example by pouring the reaction mixture onto water and/or ice, separating off the aqueous phase and isolating the ketone by distillation or crystallization.

Surprisingly, the aromatic ketones, which are useful intermediates and end products, for example for dyes, auxiliaries, crop protection agents and drugs, can be prepared by the novel process in yields which are higher than those obtained in the prior art. Furthermore, it is possible to acylate alkyl-substituted, in particular tertalkyl-substituted, aromatics without pronounced isomerization of the alkyl radical; this is particularly important in the synthesis of (tert-amylbenzoyl)-benzoic acid, since the latter is an important intermediate for the preparation of tert-amylanthraquinone, which is required for the production of hydrogen peroxide (cf. German Laid-Open Application DOS No.2,013,299).

EXAMPLE 1

Preparation of 4-tert-butylacetophenone 78 g (1 mole) of acetyl chloride in 100 ml of dichlorobenzene were initially taken, and 73 g (0.6 mole) of $AlCl_3$ were then added a little at a time. A mixture of 134 g (1 mole) of tert-butylbenzene and 60 g (0.5 mole) of diethylaluminum chloride in 50 ml of 1,2-dichlorobenzene was added dropwise to this solution at from 15° to 20° C. in the course of 5 hours. The mixture was then stirred for a further hour at 30° C.

When the reaction was complete, the reacted mixture was poured onto a mixture of 1 l of $H_2O$ with 300 g of ice and 30 ml of concentrated $H_2SO_4$, and the organic phase was separated off, dried and distilled.

Yield: 162 g (92% of theory) of 4-tert-butylacetophenone.

EXAMPLE 2

Preparation of 4-tert-amylpropiophenone

The following were reacted as described in Example 1:

92 g (1 mole) of propionyl chloride,
148 g (1 mole) of tert-amylbenzene,
27 g (0.2 mole) of $AlCl_3$ and
113 g (0.9 mole) of ethylaluminum dichloride.

Yield: 184 g (90% of theory) of 4-tert-amylpropiophenone.

EXAMPLE 3

Preparation of 2-(4'-tert-amylbenzoyl)-benzoic acid

The following were reacted in 300 ml of dichlorobenzene, as described in Example 1:

74 g (0.5 mole) of phthalic anhydride
74 g (0.5 mole) of tert-amylbenzene,
73 g (0.6 mole) of $AlCl_3$ and
63 g (0.5 mole) of ethylaluminum dichloride.

Yield: 133 g (90% of theory) of 2-(4'-tert-amylbenzoyl)-benzoic acid.

COMPARATIVE EXAMPLES 3a AND 3b

The reaction was carried out as described in Example 3, but in the presence of (a) 145 g (1.1 moles) of $AlCl_3$ in 150 ml of dichlorobenzene, without the addition of ethylaluminum dichloride, and (b) as described in Example (a) but while passing in dry air during the reaction.

When the reaction was complete, the reacted mixture was poured onto a mixture of 1 l of water with 300 g of ice and 30 ml of concentrated $H_2SO_4$, the organic phase was extracted with dilute sodium hydroxide solution, and the amylbenzoylbenzoic acids were precipitated from the aqueous phase with sulfuric acid and dried to give (a) 120.5 g and (b) 115 g of a solid which, according to HPLC analysis, had the following composition (percentages by area in HPLC):

|  | (a) | (b) |
|---|---|---|
| 2-(4-tert-amylbenzoyl)-benzoic acid | 52% | 71% |
| 2-(4-sec-amylbenzoyl)-benzoic acid | 43% | 24% |
| benzoylbenzoic acid | 2% | 2% |
| others | 3% | 3% |

EXAMPLE 4

Preparation of 2-(4'-tert-amylbenzoyl)-benzoic acid

The following were reacted in 300 ml of dichlorobenzene, as described in Example 1:
74 g (0.5 mole) of phthalic anhydride,
74 g (0.5 mole) of tert-amylbenzene,
81.3 g (0.6.mole) of AlCl$_3$ and
51.4 g (0.25 mole) of methylaluminum sesquichloride, (CH$_3$)$_3$Al$_2$Cl$_3$.

Yield: 139 g (94% of theory) of 2-(4'-tert-amylbenzoyl)-benzoic acid.

EXAMPLE 5

Preparation of 2-[4'-(1-ethyl-1-methylpentylbenzoyl)]-benzoic acid

The following were reacted as described in Example 1:
74 g (0.5 mole) of phthalic anhydride,
95 g (0.5 mole) of (1-ethyl-1-methylpentyl)-benzene,
113 g (0.85 mole) of AlCl$_3$ and
30 g (0.25 mole) of diethylaluminum chloride.

Yield: 154 g (91% of theory) of 2-[4'-ethyl-1methylpentylbenzoyl)]-benzoic acid.

EXAMPLE 6

Preparation of 2-(4'-tert-amylbenzoyl)-benzoic acid

The following were reacted as described in Example 3:
74 g (0.5 mole) of phthalic anhydride,
74 g (0.5 mole) of tert-amylbenzene,
97 g (0.8 mole) of AlCl$_3$ and
34 g (0.3 mole) of triethylaluminum.

Yield: 127 g (86% of theory) of 2-(4'-tert-amylbenzoyl)-benzoic acid.

EXAMPLE 7

74 g (0.5 mole) of phthalic anhydride in 200 ml of o-dichlorobenzene were initially taken, and 128 g (1.05 moles) of AlCl$_3$ were added a little at a time at from 15° to 20° C. A mixture of 8.3 g (0.07 mole) of diethylzinc and 74 g (0.5 mole) of tert-amylbenzene was added dropwise to the reaction solution in the course of 5 hours at this temperature. The mixture was then stirred for a further 2 hours at room temperature.

When the reaction wa$ complete, the reacted mixture was poured onto a mixture of 1l of water with 300 g of ice and 30 ml of concentrated H$_2$SO$_4$, the organic phase was extracted with dilute sodium hydroxide solution, and the amylbenzoylbenzoic acids were precipitated from the aqueous phase with sulfuric acid and dried. 133 g (90% of theory) of a mixture of 2-(4'-tert-amylbenzoyl)-benzoic acid and 2-(4'-sec-isoamylbenzoyl)-benzoic acid (teriary/secondary ratio=79:21) were obtained.

EXAMPLE 8

74 g (0.5 mole) of phthalic anhydride were reacted with 128 g (1.05 moles) of AlCl$_3$ and 25 g (0.2 mole) of diethylzinc in 74 g of tert-amylbenzene, similarly to Example 1. After the mixture had been worked up, 118 g (80% of theory) of pure 2-(4'-tert-amylbenzoyl)-benzoic acid were obtained.

EXAMPLE 9

74 g (0.5 mole) of phthalic anhydride and 134 g (1.10 moles) of AlCl$_3$ were reacted with 20 g (0.2 mole) of triethylboron in 74 g of tert-amylbenzene for 8 hours, as described in Example 1. After the mixture had been worked up in a conventional manner, 127 g (86% of theory) of a mixture of 2-(4'-tert-amylbenzoyl)-benzoic acid and 2-(4'-sec-isoamylbenzoyl)-benzoic acid (tertiary/secondary ratio=60:40) were obtained.

We claim:

1. In a process for the acylation of benzene substituted by a branched-chain amyl group, using a Friedel-Crafts catalyst selected from the group consisting of FeCl$_3$, BF$_3$, ZnCl$_2$, TiCl$_4$, aluminum bromide and aluminum chloride, to produce the corresponding amyl-substituted phenyl ketone, the improvement which comprises carrying out the acylation in the presence of an organometallic compound which is a metalalkyl or metalalkyl halide of a metal selected from the group consisting of aluminum, magnesium, boron, tin, zinc and titanium as a cocatalyst.

2. A process as claimed in claim 1, wherein a carbonyl halide or carboxylic anhydride is reacted with said benzene substituted by a branched-chain amyl group to give the corresponding amyl-substituted phenyl ketone.

3. A process as claimed in claim 2, wherein the organometallic compound is a trialkylaluminum or an alkylaluminum halide of the formula $$R_nAlX_{3-n} \qquad \text{Ia}$$

where the R groups are identical or different alkyl groups of 1 to 12 carbon atoms, X is halogen and n is 1, 2 or 3, or a mixture of said compounds.

4. A process as claimed in claim 1, wherein the organometallic compound is a metalalkyl chloride or bromide.

5. A process as claimed in claim 1, wherein the Friedel-Crafts catalyst used is aluminum chloride or bromide.

6. A process as claimed in claim 3, wherein a mixture of the Friedel-Crafts catalyst and the trialkylaluminum or alkylaluminum halide Ia is used in an amount of from 1 to 1.5 moles of the mixture per equivalent of the carbonyl halide, or in an amount of from 2 to 2.5 moles of the mixture per equivalent of the carboxylic anhydride.

7. A process as claimed in claim 3, wherein from 0.1 to about 1 mole of alkylaluminum dihalide, from 0.05 to about 0.5 mole of dialkylaluminum halide or from 0.03 to about 0.33 mole of trialkylaluminum is used per equivalent of the carbonyl halide or carboxylic anhydride.

8. A process as claimed in claim 1, wherein the benzene substituted by a branched-chain amyl group is t-amylbenzene.

9. A process as claimed in claim 8 wherein the organometallic compound is a trialkylaluminum or an alkylaluminum halide of the formula $$R_nAlX_{3-n} \qquad \text{Ia}$$

where the R groups are identical or different alkyl groups of 1 to 12 carbon atoms, X is halogen and n is 1, 2 or 3, or a mixture of said compounds.

10. A process as claimed in claim 9, wherein a carbonyl halide or carboxylic anhydride is reacted with said t-amylbenzene.

11. A process as claimed in claim 8, wherein the organometallic compound is a metalalkyl chloride or bromide.

12. A process as claimed in claim 8, wherein the Friedel-Crafts catalyst used is aluminum chloride or bromide.

13. A process as claimed in claim 10, wherein from 0.1 to about 1 mole of alkylaluminum dihalide is used per equivalent of carbonyl halide or carboxylic anhydride.

14. A process as claimed in claim 10, wherein from 0.05 to about 0.5 mole of dialkylaluminum halide is used per equivalent of carbonyl halide or carboxylic anhydride.

15. A process as claimed in claim 10, wherein from 0.03 to about 0.33 mole of trialkylaluminum is used per equivalent of carbonyl halide or carboxylic anhydride.

* * * * *